US006537818B2

(12) United States Patent
Richards et al.

(10) Patent No.: US 6,537,818 B2
(45) Date of Patent: Mar. 25, 2003

(54) SYSTEM AND METHOD OF ASPIRATING AND DISPENSING REAGENT

(75) Inventors: William Richards, Tucson, AZ (US); Anthony Ford, Tucson, AZ (US); Vince Rizzo, Tucson, AZ (US); Darin McDaniel, Tucson, AZ (US); Kurt Reinhardt, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/825,596

(22) Filed: Apr. 4, 2001

(65) Prior Publication Data

US 2001/0010936 A1 Aug. 2, 2001

Related U.S. Application Data

(62) Division of application No. 09/259,238, filed on Feb. 26, 1999, now Pat. No. 6,405,609.
(60) Provisional application No. 60/076,198, filed on Feb. 27, 1998.

(51) Int. Cl.$^7$ .......................... G01N 35/08; G01N 1/10; G01N 21/00; G01N 1/00; B01L 3/02; B01L 3/00
(52) U.S. Cl. .......................... 436/54; 436/180; 422/100; 422/81; 422/102; 73/863.32; 73/864; 73/864.01; 73/864.11; 73/864.31
(58) Field of Search .......................... 422/81, 100, 102; 436/180, 54; 73/864, 863.32, 864.01, 864.11, 864.31

(56) References Cited

U.S. PATENT DOCUMENTS

| 4,286,637 | A | * | 9/1981 | Wilson ..................... 141/374 |
|---|---|---|---|---|
| 4,539,855 | A | * | 9/1985 | Jacobs |
| 4,577,514 | A | * | 3/1986 | Bradley et al. .......... 73/863.01 |
| 4,895,706 | A | * | 1/1990 | Root et al. .................. 422/102 |
| 4,902,481 | A | * | 2/1990 | Clark et al. .................. 422/101 |
| 5,035,866 | A | * | 7/1991 | Wannlund .................... 422/102 |
| 5,116,496 | A | * | 5/1992 | Scott |
| 5,304,347 | A | * | 4/1994 | Mann et al. |
| 5,334,353 | A | * | 8/1994 | Blattner |
| 5,356,814 | A | * | 10/1994 | Carrico et al. ........... 435/283.1 |
| 5,512,248 | A | * | 4/1996 | Van ............................. 422/100 |
| 5,525,302 | A | * | 6/1996 | Astle |
| 5,525,515 | A | * | 6/1996 | Blattner |
| 5,578,455 | A | * | 11/1996 | Tosa et al. .................. 435/7.32 |
| 5,629,201 | A | * | 5/1997 | Nugteren et al. |
| 5,639,665 | A | * | 6/1997 | Arai et al. |
| 5,736,105 | A | * | 4/1998 | Astle |
| 5,861,094 | A | * | 1/1999 | Goehde ....................... 210/232 |
| 6,054,099 | A | * | 4/2000 | Levy |
| 6,183,645 | B1 | * | 2/2001 | DeWitt et al. .............. 210/634 |
| 6,296,764 | B1 | * | 10/2001 | Guirguis et al. ......... 210/323.1 |
| 6,372,144 | B1 | * | 4/2002 | Vassarotti ................... 210/650 |
| 2001/0004449 | A1 | * | 6/2001 | Suzuki et al. |
| 2001/0016358 | A1 | * | 8/2001 | Osawa et al. |
| 2001/0055545 | A1 | * | 12/2001 | Takii et al. |
| 2002/0037239 | A1 | * | 3/2002 | Komatsu .................... 422/100 |

* cited by examiner

Primary Examiner—Jill Warden
Assistant Examiner—Brian R Gordon
(74) Attorney, Agent, or Firm—McDonnell Boehnen Hulbert & Berghoff

(57) ABSTRACT

Apparatus and methods for aspirating and dispensing reagents are provided. Aspirating of reagents is accomplished by a probe, a vial insert and reagent vial according to the present invention wherein a seal is formed between the probe and the vial insert when the probe engages the vial insert. Dispensing of reagents is accomplished by a probe and a probe dispense and wash station according to the present invention wherein a seal is formed between the probe and the vial insert when the probe engages the probe dispense and wash station.

33 Claims, 11 Drawing Sheets

PROBE ENGAGED WITH REAGENT VIAL INSERT

PROBE ENGAGED WITH DISPENSE AND WASH STATION

PROBE ENGAGED WITH REAGENT VIAL INSERT

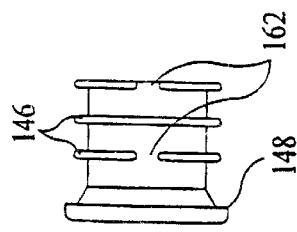
FIG. 4B
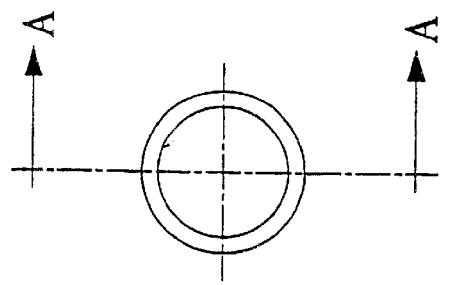
FIG. 4A
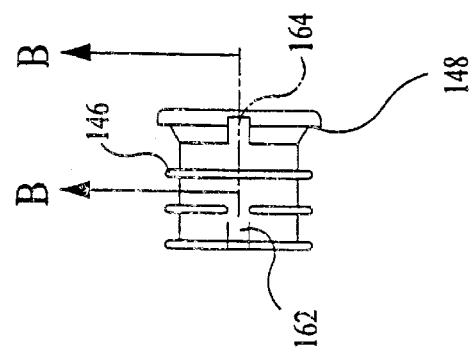
FIG. 4C
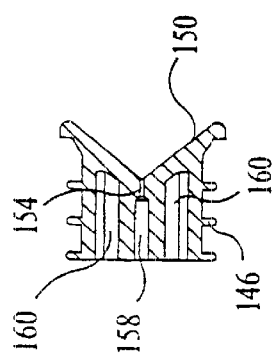
FIG. 4D SECTION A-A
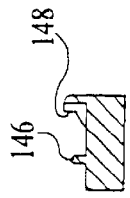
FIG. 4F
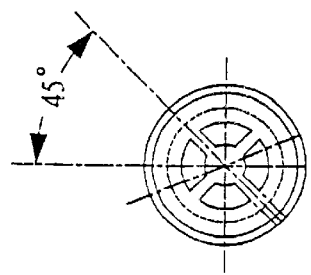
FIG. 4E SECTION B-B

SYSTEM AND METHOD OF ASPIRATING AND DISPENSING REAGENT

REFERENCE TO RELATED APPLICATIONS

This application is a divisional of U.S. patent application Ser. No. 09/259,238 filed Feb. 26, 1999, now U.S. Pat. No. 6,405,609, claims priority benefits under 35 U.S.C. §119(e) to U.S. provisional application Ser. No. 60/076,198 filed on Feb. 27, 1998. This application also hereby incorporates by reference U.S. provisional application Ser. No. 60/076,198 filed on Feb. 27, 1998 in its entirety.

BACKGROUND OF THE INVENTION

A. Field of the Invention

This invention relates generally to the fields of histology and cytology, and more particularly relates to a method and apparatus for aspirating and dispensing reagent.

B. Description of Related Art

Reagents are used in a variety of devices in the fields of histology and cytology. For example, one device which uses reagents is a histochemical staining device. Histochemical staining is a useful tool in histological diagnosis and the study of tissue morphology. Histochemical "Special Stains" require a series of treatment steps conducted on a tissue section mounted on a glass slide to highlight by selective staining certain morphological indicators of disease states. Typical steps may include pretreatment of the tissue section to facilitate staining, application of various dyes to stain morphological structures, clarifiers to remove unreacted dye, differentiating agents, counterstains, and the like. Each of these steps is separated by multiple rinse steps to remove unreacted residual reagent from the prior step. Incubations are conducted at elevated temperatures, usually around 60° C., and the tissue must be continuously protected from dehydration. Other devices that use reagents as part of its processing include Immunohistochemical stainers, devices that perform in-situ hybridization of DNA/RNA, stainers that perform enzymatic tissue stains, and hemtoxylin and eosin (H & E) stainers.

In order to introduce reagents and other fluids during processing, a reagent delivery system and method is used. Typically, the regent delivery system automatically pippettes reagents by inserting a needle or plastic tube into the reagent reservoir or vial, drawing up the reagent into the tube with a motor driven syringe, moving the needle to the slide (or other receptacle) and reversing the syringe to dispense the reagent. Such typical designs have the drawback that the vials are open, exposing the reagent to the atmosphere, permitting evaporation and potentially reducing reagent reactivity due to oxygen exposure. Moreover, open vials are vulnerable to spills resulting in loss of reagent and operator exposure.

SUMMARY OF THE INVENTION

The present invention is directed to an apparatus and method for applying reagent to slides for histochemical or cytological analysis. As part of thes analyses, different types of reagents are applied to tissue sections placed on slides. The tissue sections are then viewed by a medical practitioner who reads the slide for purposes of patent diagnosis, prognosis or treatment selection. More specifically, the apparatus is a staining instrument that automatically applies chemical and biological reagents to tissue or cells mounted or affixed to standard glass microscope slides. Each slide receives the selected reagents which are dispensed from reagent vials.

Obtaining of reagents is accomplished through a unique reagent dispense system that comprises a probe, a vial insert and a reagent vial. The vial insert is attached to the reagent vial. The vial insert is also contacted with at least a portion of the probe to form a seal wherein reagent is withdrawn from the reagent vial. Dispensing of reagents is accomplished by a probe and a probe dispense and wash station. The probe contacts at least a portion of the probe dispense and wash station to form a seal in order to dispense reagent and in order to clean the probe.

A key advantage of the present invention is to provide a system that aspirates reagents from a vial while minimizing evaporation in the reagent vial.

Another advantage of the present invention is to provide a system that dispenses reagents accurately.

Still another advantage of the present invention is to provide a system that minimizes cross-contamination of the reagent vials through cleaning of the reagent delivery system.

With the foregoing and other objects, advantages, and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

A presently preferred embodiment of the present invention is described herein with reference to the drawings wherein:

FIG. 1c is a block diagram of the biological reaction system as disclosed in FIG. 1a;

FIG. 4a is a top view of the vial insert as shown in FIG. 3;

FIG. 4b is a cross-sectional view at section A—A of FIG. 4a;

FIG. 4c is a left side view of the vial insert as shown in FIG. 3;

FIG. 4d is a right side view of the vial insert as shown in FIG. 3;

FIG. 4e is a cross-sectional view at section B—B of FIG. 4d;

FIG. 4f is a bottom view of the vial insert as shown in FIG. 3;

DETAILED DESCRIPTION OF PREFERRED AND ALTERNATIVE EMBODIMENTS OF THE INVENTION

Figure 1A:
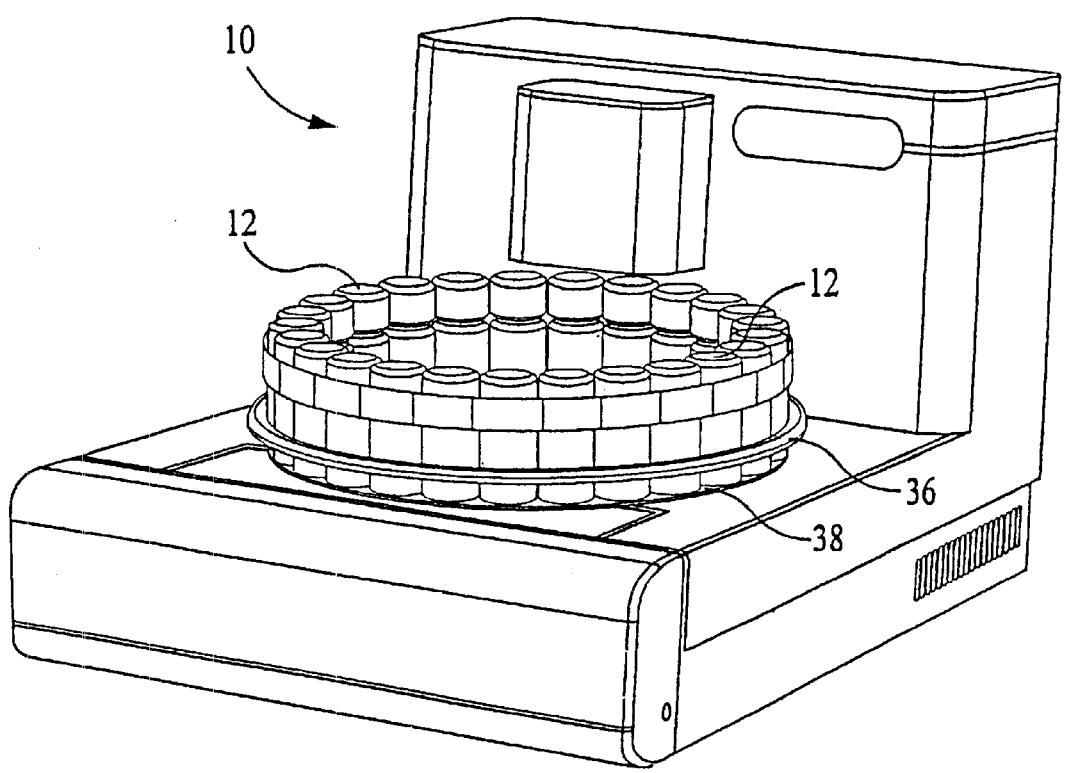
FIG. 1a is a perspective view of a biological reaction system showing a reagent carousel, reagent tray, and reagent vials according to an embodiment of the invention.

Referring now in detail to the drawings wherein like parts are designated by like reference numerals throughout, there is illustrated in FIG. 1a a perspective view of a histopathology apparatus according to the present invention which is designated generally by reference numeral 10. This is merely one example of a device which uses reagents during processing. Apparatus 10 is designed to automatically stain or otherwise treat tissue mounted on microscope slides with reagents associated therewith in the desired sequence, time and temperature. Other devices which may use reagents in the course of processing include Immunohistochemical stainers, devices that perform in-situ hybridization on DNA/RNA, stainers that perform enzymatic tissue stains, and hemtoxylin and eosin (H & E) stainers. Tissue sections so stained or treated are then to be viewed under a microscope by a medical practitioner who reads the slide for purposes of patient diagnosis, prognosis, or treatment selection. A preferred configuration of apparatus 10, as well as system 12, is generally described in U.S. patent application Ser. No. 08/909,335 (pending) filed on Aug. 11, 1997 by inventors Druyor-Sanchez et al., and in U.S. patent application Ser. No. 08/995,052 (pending) filed on Dec. 19, 1997 by inventors Druyor-Sanchez et al., both of which is also hereby incorporated by reference, except with respect to the novel reagent aspirate/delivery system, as disclosed below.

Figure 1B:
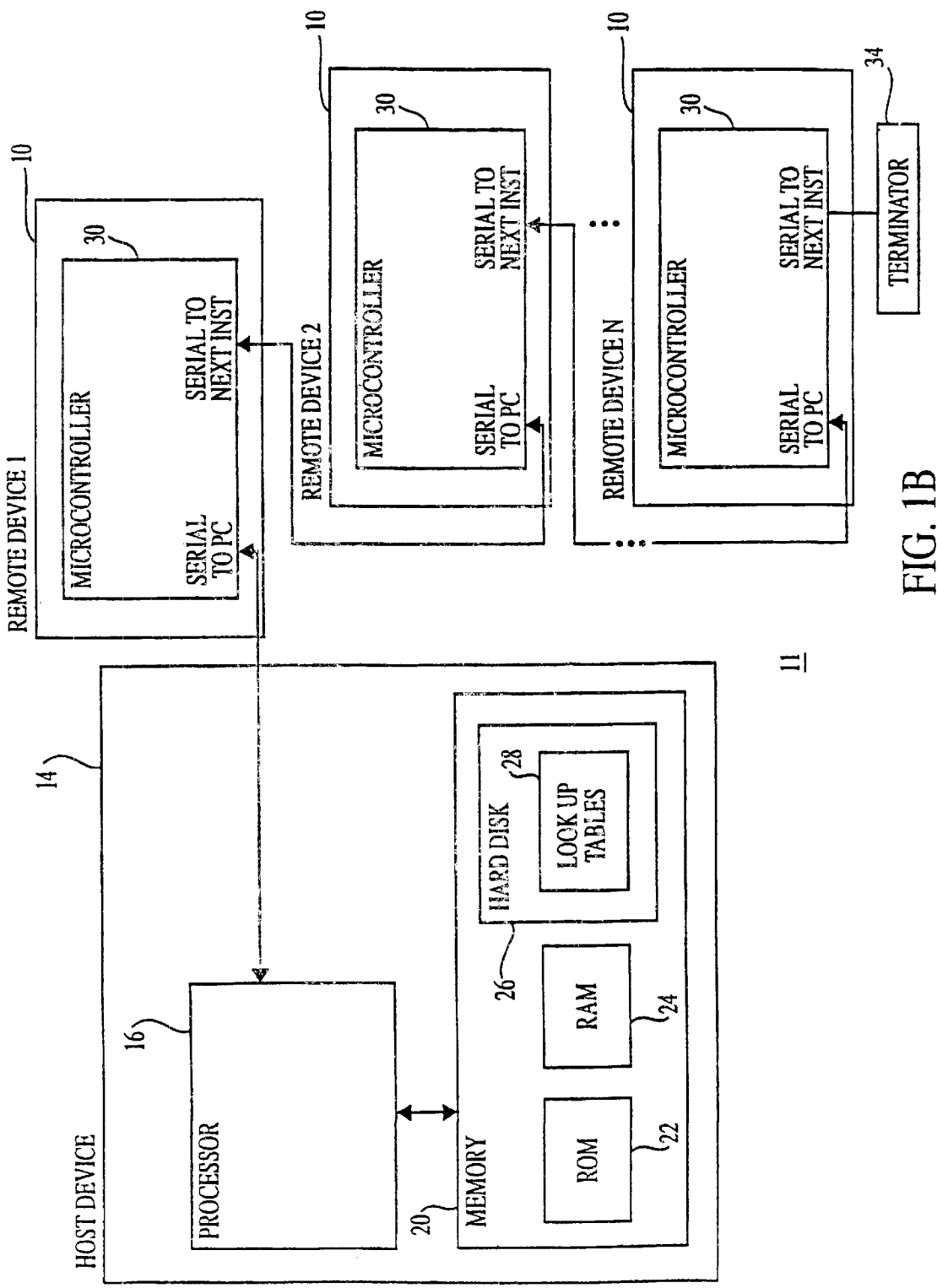
FIG. 1b is a block diagram of the host and reagent

In a preferred embodiment, apparatus 10 functions as one component or module in a system 11, as shown in FIG. 1b, which includes a host device 14. The host device 14 is a typical personal computer with a processor 16. The processor 16 is also in communication with memory devices 20, including non-volatile memory devices such as a ROM 22, volatile memory devices such as a RAM 24, and a hard disk 26. Any of the memory devices may contain databases or look-up tables; however, in the preferred embodiment, the hard disk 26 contains the databases or look-up tables 28. The remote device 10 includes a processor, such as a microcontroller 30 wherein the microcontroller 30. In an alternative embodiment, the microcontroller 30 in the remote device 10 is replaced by a personal computer. The microcontroller 30 is manufactured by Dallas Semiconductor, model number DS2251T 128K Soft microcontroller module. The microcontroller 30 has two lines (serial to PC, serial to next inst) to facilitate communication between the host and the remote devices. As shown in FIG. 1b, the host device 14, through the processor 152, is connected to the serial to PC pin of the microcontroller 30 of remote device 1 (10). The serial to next inst line of the microcontroller 30 of remote device 1 (10) is connected to the serial to PC pin of remote device 2 (10). The connections follow similarly through remote device N (10). In the preferred embodiment, there are up to 8 remote devices on the network. In order to terminate the network with the correct impedance in order to avoid any pulse reflections on the network, the serial to next instrument line is connected to a terminator 34. The terminator 34 can thereby match the impedance of the network. In the event that one of the remote devices on the network must be removed from the network, the serial to PC line and the serial to next remote device line need only be connected to each other for the remote device 10 to be removed from the network. Thereby, the network does not "see" that remote device 10 and is effectively removed from the network.

Figure 1C:
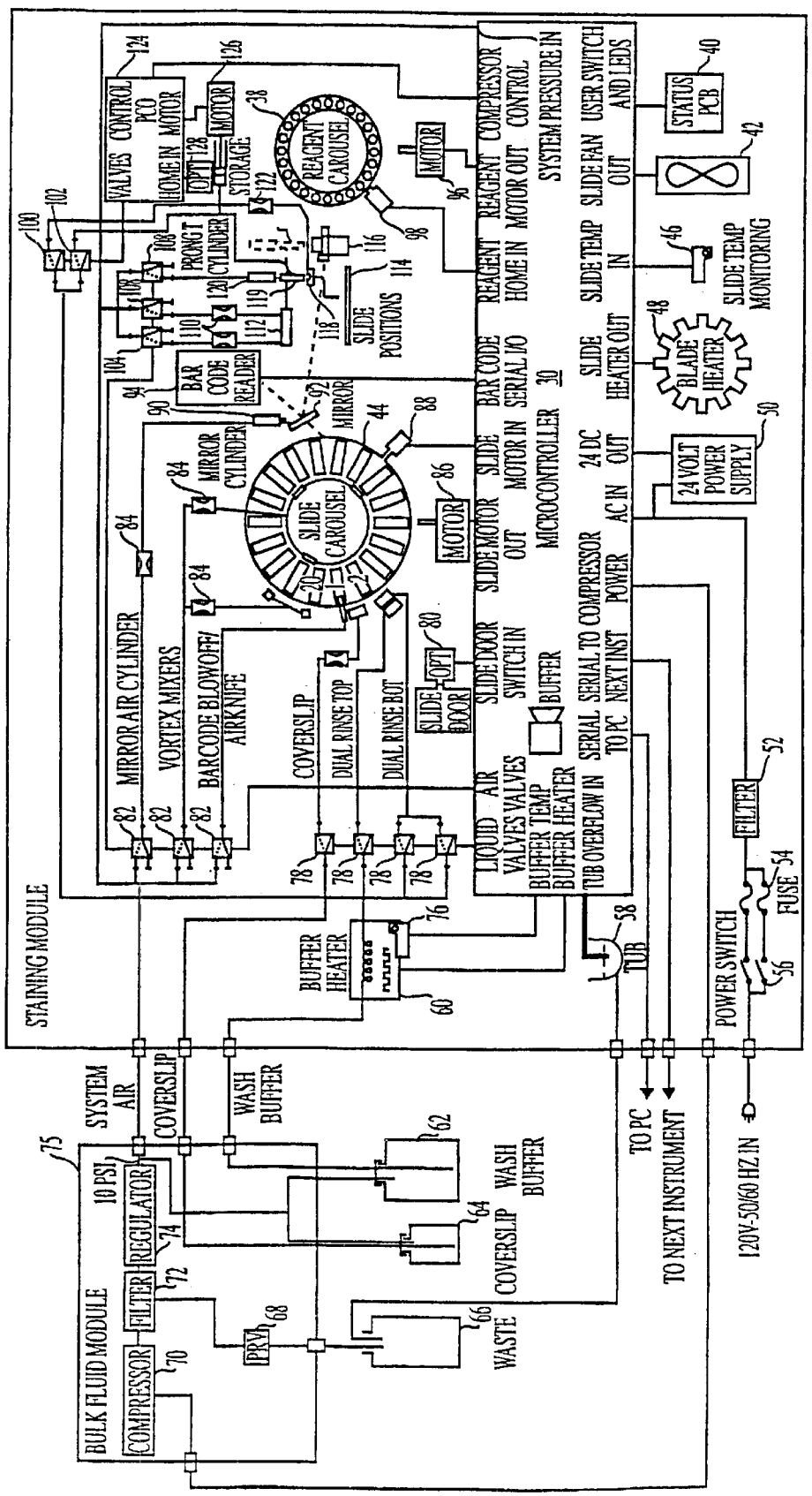

Referring to FIG. 1c, there is shown an expanded block diagram of the remote device as disclosed in FIG. 1a. As discussed previously, the remote device 10 includes a microcontroller 30. The microcontroller 30 has a user switch and LEDs line which connects to the status PCB (printed circuit board) 40. The status PCB 40 is the interface to the user for the remote device 10 and includes three LEDs (light emitting diodes) for power determination, error notification and notification of a run in progress.

The microcontroller 30 also has a slide fan out connection which is used to control the blower fan 42. The blower fan 42 recirculates air to heat the slides on the slide carousel 44 of the remote device 10 by forcing air over the heater 48 and then over the slides. The slide temp in connection on microcontroller 30 is connected to the slide temperature monitoring sensor 46 which senses the temperature of the air. The slide temperature monitoring sensor 46 is positioned in the path of the heated air and thereby sends information to the microcontroller 30 when to turn the slide heater 48 on and off. The slide heater out connection is connected to the slide heater 48 which, as discussed previously, heats the air in order to elevate the temperature of the slides. The host device 14 downloads to the remote device 10 both the sequence of steps in a run program, and the sensor monitoring and control logic called the run rules. One of the environmental parameters is the upper and lower limit of the air temperature of the slides (used for heating the slides). If, during a run, the environmental temperature is below the lower limit, as indicated by slide temperature monitoring sensor 46, the slide heater 48 is turned on. Likewise, if the environmental temperature is above the upper limit, as indicated by slide temperature monitoring sensor 46, the slide heater 48 is turned off. The power supply 50 supplies both 24 VDC and 5 VDC to the applicable 24 VDC and 5 VDC connections. The 24 Volt power supply 50 is used to power the motors 86, 96, 126 which move the slide carousel 44 and the reagent carousel 38, and the syringe 28. The 120 VAC input is sent through a power switch 56, a fuse 54 and a filter 52 to the AC In connection of the power supply 50. The 120 VAC input is also used to power the slide heater 48, buffer heater 60 and compressor 70 of the bulk fluid module, which are described subsequently. The serial to PC line and the serial to next remote device line are described with reference to FIG. 1b.

In order to control the temperature of the block, a buffer heater temperature sensor 76 is used which is physically placed on the aluminum block. The microcontroller 30 receives the buffer temperature sensor input via the buffer temp line and can thereby control the temperature of the buffer heater 60 by turning on and off the buffer heater 60 via the buffer heater line on the PCB microcontroller 30.

The fluid valves 78 for the Liquid Coverslip™ and the wash buffer are controlled by the fluid valve connections. There is a separate pair of wires (power and ground) for each valve 78 shown in FIG. 1c which are omitted for ease of display. Each valve 78 is a relay which is activated by the microcontroller 30. Further, there is a slide door optical sensor 80 which is input to the slide door switch in line connection and which is used to determine if the front door of the remote device 10 is open. This sensor 80 is used for safety reasons so that, if the front door is open and remains open for five minutes, the slide carousel 44 does not move.

Motors 86, 96 move the slide carousel 44 and the reagent carousel 38, and are connected to the slide motor out connection and the reagent motor out connection, respectively. The motors 86, 96 are typically stepper motors. Sensors 88, 98 are placed in proximity to the slide carousel 44 and the reagent carousel 38 in order to determine the "home" position of each. In the case of the slide carousel 44, the slide carousel home sensor 86 is inductive-type and senses a piece of metal placed underneath the slide designated as the "home" position. When the "home" position is found, the sensor 88 sends a signal to the slide home in line of the microcontroller 30. In the case of the reagent tray 36, the sensor 96 also is an inductive-type of sensor. The reagent tray 36 has a large flat metal ring around the entire tray except for the home position. In this manner, when the sensor 96 senses an absence of metal, this is determined to be the home position thereby indicating to the microcontroller 30, via the reagent home in connection, that the home position is found. The sensor 96 senses the reagent tray 36, rather than the reagent carousel 38, since the user may remove the reagent tray 36. Additionally, since the sensor 96 looks for the absence of metal for the home position, the absence of the reagent tray 36 may be tested by looking for the absence of metal in two consecutive positions.

System pressure is determined via the system air line which directly feeds into a transducer. As shown in FIG. 1c, the bulk fluid module 75 includes the compressor 70 which pressurizes the air to up to 90 psi. The compressed air is sent to a filter 72 in order to filter out water and other contaminants. Pressure is regulated in a two-step fashion. First, the pressure is regulated at the compressor to approximately 25 psi (±1 psi) via a spring diaphram (prv) 68. The prv 68 is manufactured by Norgren in Littleton, Colo., part number NIP-702 with a plastic bonnet. Second, the pressure is fine-tuned to 13 psi using an air pressure regulator 74. The pressure regulator 74 is very accurate in terms of precise pressure regulation over long periods of time. In this manner, the compressor 70 need not overwork itself since the prv 68 maintains the pressure at the output of the compressor to 25 psi by opening and letting out excess pressure when the pressure exceeds 25 psi. Water and particulates, which are filtered out of the air via the filter 72, are sent to a waste receptacle. The compressed air pressurizes the Liquid Coverslip™ and wash buffer bottles 64, 62 so that when the valves 78 are opened corresponding to the Liquid Coverslip™, volume adjust, dual rinse top, dual rinse bottom lines, the pressure is already on the line and the fluid may flow. The compressed air is used for the dispense cylinder extend line, the dispense cylinder retract line, the mirror air cylinder line, the vortex mixers line, and the bar code blowoff/airknife line. The compressed air is also used for the probe out air valve 104, probe in air valve 106, and probe air down valve 108, as described subsequently.

The mirror air cylinder line is used to turn the mirror cylinder 90 so that the bar code reader 94 either reads bar codes on the slides of the slide carousel 44 or bar codes on the fluid dispensers on the reagent carousel 38. The output from the bar code reader 94 is input to the microcontroller 30 via the bar code serial I/O connection. In between the valve 82 for the mirror air cylinder line and the mirror cylinder is a flow restrictor 84. The flow restrictor 84 slows the flow of air in the line while still maintaining the 13 psi pressure on the line. In this manner, this moves the mirror slower than would otherwise be done without the restrictor 84.

Reagent Delivery System

Figure 2:
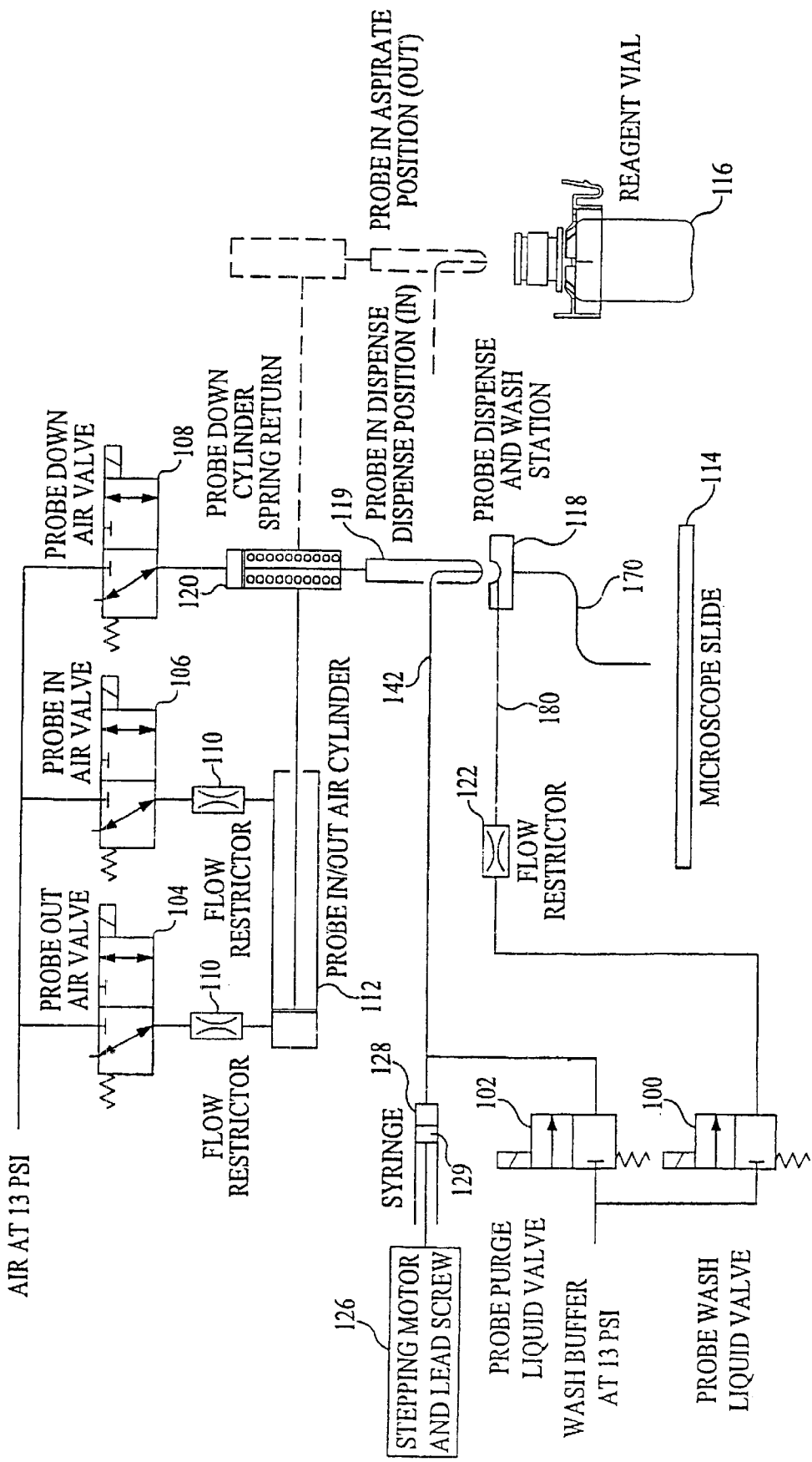
FIG. 2 is a diagram of the reagent delivery system as disclosed in FIGS. 1a and 1b.

As shown in FIG. 1c and in more detail in FIG. 2, the reagent dispense system includes a reagent carousel 38, reagent vials 116, reagent vial inserts 132, reagent aspirate/dispense probe 119, probe motion control components (in the form of valves 104, 106, 108, air cylinders 112, 120 and restrictors 110), a motor driven syringe pump (in the form of a motor 126 and syringe 128), and control elements (in the form of a dispense control printed circuit board 124 and microcontroller 30). The reagent carousel 38 is moved via a motor 96, which is controlled by the microcontroller 30 through the reagent motor out line. The reagent delivery system uses a syringe 128 to move reagents from reagent vials 116 to the slides 114. As shown in FIG. 1c, the slide which is in the reagent dispense position is slide position 2. Slide position 2 corresponds to the slide denoted by "2" on the slide carousel 44. The reagent vials 116 are standard plastic vials that are used to package reagents. The microcontroller 30 controls the motion of the probe 119 via control of the air cylinders by the system pressure in line. The microcontroller 30 also controls the cleaning of the probe 119 and probe dispense & wash station 118, as described subsequently via the dispense control pcb 124. The microcontroller sends control signals via the dispense control line to the dispense control pcb 124. The dispense control pcb 124 controls the valves 100, 102 which channel wash buffer to the probe 119 and probe dispense & wash station 118. The dispense control pcb 124 further controls the motor 126 which is connected to the plunger of the syringe 128. In order for the dispense control pcb 124 to determine the position of the syringe 128, there is an optical sensor 130 which is activated when the syringe is in the home position.

In a preferred embodiment, the probe motion control components include air cylinders 112, 120. The air cylinders 112, 120 produce a piston-like motion, moving the probe 119 in all necessary directions including the 'Z' and 'θ' directions. For example, probe in/out air cylinder 112, in combination with probe out air valve 104 and probe in air valve 106, control the movement of the probe 119 in the horizontal direction. The probe out air valve 104 and the probe in air valve 106 are pressurized using air at 13 psi. The outputs of the probe out air valve 104 and the probe in air valve 106 are connected to flow restrictors 110, which are in turn connected to the probe in/out air cylinder 112. The microcontroller 30 controls the opening and closing of the probe out air valve 104 and the probe in air valve 106 so that movement of the probe 119 in the horizontal direction may be controlled. In addition, flow restrictors 110 are used to control the flow of pressurized air from the valves 104, 106 to the probe in/out air cylinder 112. In practice, the probe in/out air cylinder 112 may move the probe 119 from above the probe dispense & wash station 118 and the reagent vial 116.

In addition, movement in the 'Z' direction is controlled by the probe down air valve 108 in combination with the probe air cylinder with spring return 120. Air pressurized at 13 psi is connected to the probe down air valve 108. The output of the probe down air valve 108 is connected to the probe air cylinder with spring return 120. The microcontroller 30 controls the opening and closing of the probe down air valve 108 so that, upon activation of the probe down air valve 108, the probe air dispense cylinder 120 pushes the probe 119 downward. Therefore, upon closing of the probe down air valve 108, the probe air cylinder 120 is retracted by the spring return.

In practice, the probe 119 is in the dispense position when the probe 119 is inserted into the probe dispense & wash station 118, as described subsequently. Moreover, the probe 119 is in the aspirate position when the probe 119 is inserted into the vial insert 132, also described subsequently. Therefore, a variety of air cylinders may be used including air cylinders to push in and push out and air cylinders in combination with spring return. In an alternate embodiment, the probe may be moved by using a variety of force mechanisms such as a motor, solenoid or a piston.

The syringe 128 aspirates and dispenses reagent via a motor 126, as shown in FIG. 2. The syringe is manufactured by Hamilton Corporation, Model Gastight and whose plunger 129 is connected to a lead screw 126 which is rotated by a stepping motor. Tubing 142 is also connected to the probe, as described subsequently. The microcontroller 30, via the dispense control pcb 124, controls the stepping motor and lead screw 126 so that when the probe 119 is in the aspirate position (i.e., inserted into the vial insert 132), the stepping motor and lead screw 126 drive the plunger 129 of the syringe 128 to withdraw reagent from the reagent vial 116. The microcontroller 30 also controls the stepping motor and lead screw so that when the probe 119 is in the dispense position (i.e., inserted into the probe dispense & wash station 118), the stepping motor and lead screw drive 126 the plunger 129 of the syringe 128 to force reagent from the syringe 128 and from the tubing 142 into the probe dispense & wash station 118, through additional tubing 170 and onto the microscope slide 114. In an alternative embodiment, the syringe may be driven to aspirate or dispense reagent through a variety of methods including air cylinders, solenoids or any other means to move the plunger of the syringe.

Figure 3:
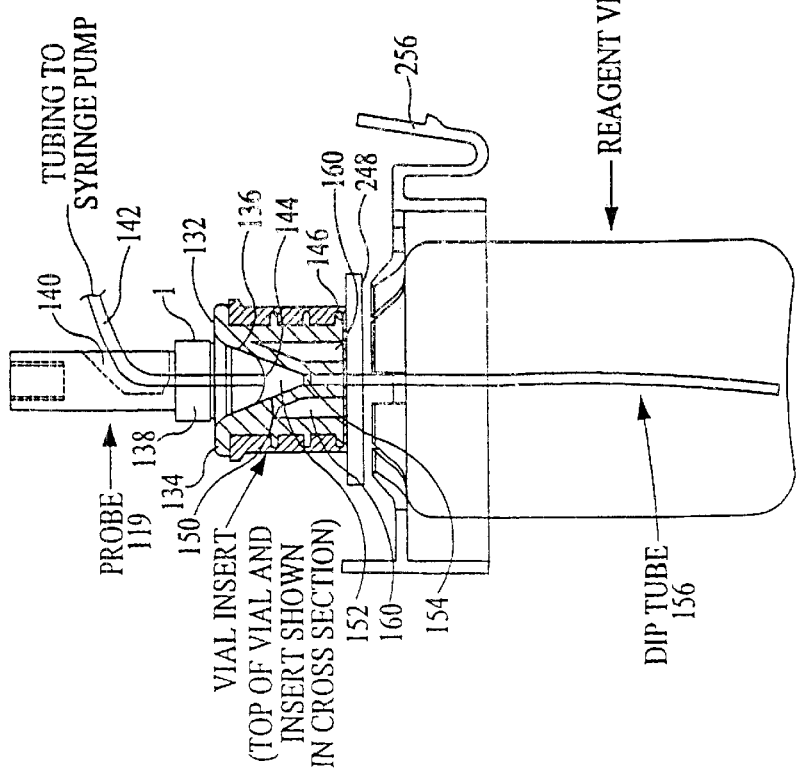
FIG. 3 is a front cross-sectional view of the probe, vial insert and reagent vial for the reagent delivery system of FIG. 2.

Referring to FIG. 3, there is shown a front cross-sectional view of the probe 119, vial insert 132 and reagent vial 116 for the reagent delivery system of FIG. 2. The probe is, in a preferred embodiment, a cylindrical object made of stainless-steel with one end being a shaped surface. In a preferred embodiment, the one end is curved in the form of a hemisphere. The vial insert 132 is-composed of a pliable material such as SANTOPRENE™. The probe and the vial insert may be composed of any substances which form a seal, as described subsequently, when the vial insert 132 and the probe 119 contact. For example, one or both of the probe and the vial insert may be composed of a soft, pliable material. Alternatively, the probe may be composed of a rubber-type of material and the vial insert may be composed, in part, of stainless-steel.

The probe 119 is milled at one portion so that an o-ring 134 may be snapped into the milled portion of the probe 119. In a preferred embodiment, the o-ring 134 is composed of a pliable material such as KALREZ™ by Dupont. At both ends of the o-ring 134 are o-ring holders 136, 138 in order to hold the o-ring 134 in place. As described subsequently in more detail, the probe 119 and vial insert 132 contact each other to form a seal. So that, the probe may be any form with one end that forms a seal between at least a portion of one surface of the probe 119 and at least one portion of the vial insert 132. In a preferred embodiment, the seal formed is annular. The probe further has a hollow portion 140 for receiving the tubing 142 to the syringe 128. In a preferred embodiment, the tubing is threaded to a hole 144 at one end of the probe 119.

Referring to FIGS. 4a–f, there is shown a top view, a cross-sectional view at section A—A, a left side view, a right side view, a cross-sectional view at section B—B and bottom view of the vial insert 132 as shown in FIG. 3. The vial insert 132 is pressed into the top portion of the reagent vial with ribs, that are formed around the circumference or outer surface of the vial insert 132, deforming in order to tightly fit the vial insert 132 in the opening of the reagent vial 116. In addition, the top portion of the vial insert has a seat 148 with abuts against the top portion of the reagent vial. The vial insert 132 also has an upper surface 150 which is shaped. In the preferred embodiment, the upper surface is a curved surface that is funnel-like. When the probe engages the vial insert 132, a portion of the upper surface 150 mates with at least a part of the lower portion of the probe. In a preferred embodiment, the upper surface of the vial insert contacts the portion on the probe below the o-ring, as shown in FIG. 3a. In an alternative embodiment, a portion of the funnel-like curved surface may engage any portion of the probe, including the o-ring.

Upon contact or engaging of the probe with the vial insert 132, a seal is formed so that when withdrawing reagent, air does not leak from the upper surface 150 of the vial insert, as described subsequently. In a preferred embodiment, the conical shape of the upper surface of the vial insert in contact with the lower spherical-shaped portion of the probe forms a cavity 152. The cavity 152, in a preferred embodiment is funnel-shaped so that any reagent left in the vial insert 132 will flow back down into the vial 116 when the probe is removed. In an alternative embodiment, the upper surface is a curved surface that is hemispherical, so that a larger percentage of the surface area of the curved end of the probe abuts the upper surface. However, again in order to avoid capillary action, the surface area of contact between the probe and the vial insert 132 should be kept to a minimum while still avoiding an air leak between the probe 119 and the vial insert 132.

The vial insert 132 is molded so that the lowest portion of the upper surface includes a vial transition area 154. The vial transition area 154, in a preferred embodiment, is integral with the main body of the vial insert 132. In an alternate embodiment, the vial transition area may be composed of a separate piece which is snapped into the main body of the vial insert. The vial transition area 154 is adjacent to the dip tube 156, which is composed of Teflon® tubing and which fits in the molded lower portion of the vial insert. The dip tube 156 has an inner diameter and an outer diameter, which in the preferred embodiment is $\frac{1}{32}$" and $\frac{1}{16}$", respectively. In a preferred embodiment, the diameter of the vial transition area 154 should equal the inner diameter of the dip tube 156. Thus, when the dip tube 156 is inserted into the cavity 158 adjacent to the vial transition area 154, it results in a smooth transition between the vial transition area 154 and the dip tube 156. Therefore, the diameter of the vial transition area is $\frac{1}{32}$". In this manner, reagent will not be trapped in the vial transition area 154 or in the dip tube 156. And, the small vial transition area 154 reduces evaporation of the reagent. The vial insert is also molded with cavities 160 in order for the vial insert to be molded with accuracy.

In operation, the probe 119 is inserted into the vial insert 132, the plunger 129 of the syringe 128 is withdrawn and reagent is drawn from the vial 116. In a preferred embodiment, the hole 144 for the lower portion of the probe lines up with the vial transition area, as shown in FIG. 3. In an alternate embodiment, the hole 144 need not line up with the vial transition area 154. Reagent may still travel as long as a seal between the probe 119 and the vial insert 132 is maintained.

In order to equalize the pressure in the reagent vial 116 while withdrawing reagent, a pathway for air to travel from outside the vial and the vial insert 132 is included. In a preferred embodiment, the pathway is formed by breaks 162 in the ribs, as shown in FIGS. 4c and 4d. Moreover, there is a break 164 in the upper portion of the vial insert in order to form a path to outside of the vial insert. In a preferred embodiment, the breaks 162 in the ribs are formed for the air to travel in a circuitous path around the vial insert 132. In this manner, the pathway allows for the equalization of pressure while still minimizing spillage, if the reagent vial is tipped over, due to the circuitous path. Other pathways may include spirals or helixes.

Figure 5:
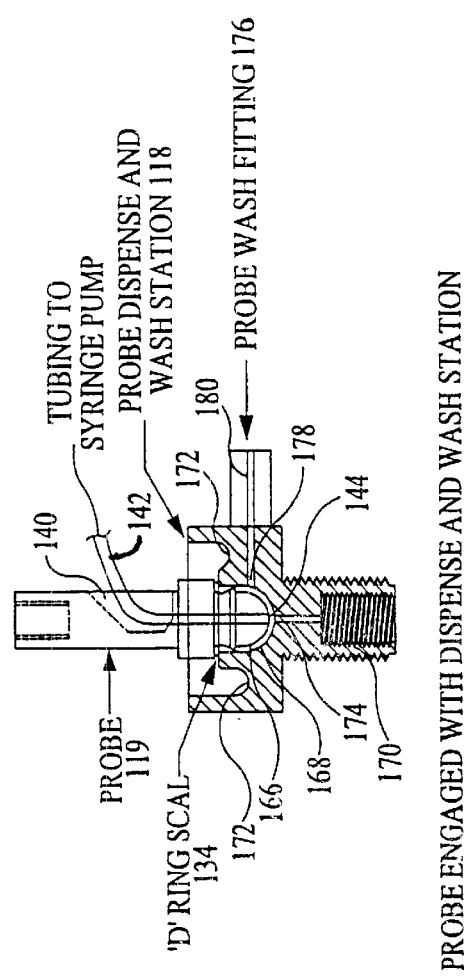
FIG. 5 is a front cross-sectional view of the a probe and probe dispense & wash station for the reagent delivery system of FIG. 2.

FIG. 5 is a front cross-sectional view of the a probe 119 and probe dispense & wash station 118 for the reagent delivery system of FIG. 2. The probe dispense & wash station 118 has an upper surface 168, as described subsequently, wherein at least a portion of the upper surface 168 engages at least a portion of the probe 119 to form a seal. This seal allows for the dispensing of reagent from the tubing 142 to the probe dispense & wash station 118. The probe 119 and the probe dispense & wash station 118 may be composed of any substances which enable a seal to form when the probe dispense & wash station 118 and the probe 119 contact. For example, both the probe 119 and the probe dispense & wash station 118 may be composed of a plastic or rubberized material. In a preferred embodiment, the probe dispense & wash station 118 is composed of stainless steel. And, the point of contact is between the o-ring 134 and a portion of the upper surface 168 of the probe dispense & wash station, as shown in FIG. 5.

The upper surface 168 of the probe dispense & wash station may be any shape as long as a seal is formed between the probe 119 and the probe dispense & wash station 118. In the preferred embodiment, the upper surface 168 of the probe dispense & wash station 118 should mate with the lower portion of the probe 166 to form an annular seal. Since the lower portion of the probe 166 is spherical in shape, the upper surface 168 of the probe dispense & wash station is also spherical in shape. In practice, the diameter of the upper surface 168 is slightly larger than the diameter of the curved lower portion 166 of the probe. So that, the point of contact between the probe 119 and the probe dispense & wash station 118 in the preferred embodiment is between a portion of the upper surface and the o-ring 134 that forms the annular seal. And, to minimize reagent left in the probe dispense & wash station, the volume between the upper surface 168 of the probe dispense & wash station and the lower portion 166 of the probe is kept to a minimum.

In operation, after the probe 119 contacts with the probe dispense & wash station 118, reagent is dispensed from tubing 142 to the probe dispense & wash station 118. In a preferred embodiment, the hole 144 for the lower portion of the probe lines up with the hole 174 in the upper surface 168 of the probe dispense & wash station 118. In an alternate embodiment, the hole need not line up with the hole in the upper surface of the probe dispense & wash station 118. Reagent may still travel as long as a seal between the probe 119 and the probe dispense & wash station 118 is maintained. In addition, the lower portion of the probe dispense & wash station includes a screw fitting 170 for holding the Teflon® tubing 170.

In order to avoid spillage of reagent (in the cases where the seal between the probe and the probe dispense & wash station is faulty and during washing of the probe and the probe dispense & wash station, as described subsequently), there is a trough 172 formed within the probe dispense & wash station 118. The trough 172 acts to catch reagent, which spirals downward and empties outside of the probe dispense & wash station 118.

As described subsequently, the probe 119 and probe dispense & wash station 118 are washed after dispensing of reagent. For the washing, a probe wash fitting 176 holds tubing 180 which is connected, via a hole 178, to the upper surface 168 of the probe dispense & wash station 118. The hole may be placed at any portion of the upper surface 168 of the probe dispense & wash station 118. In a preferred embodiment, the hole 178 is placed between the juncture at o-ring 134 and the hole 174 to the tubing, as shown in FIG. 5.

Figure 6:
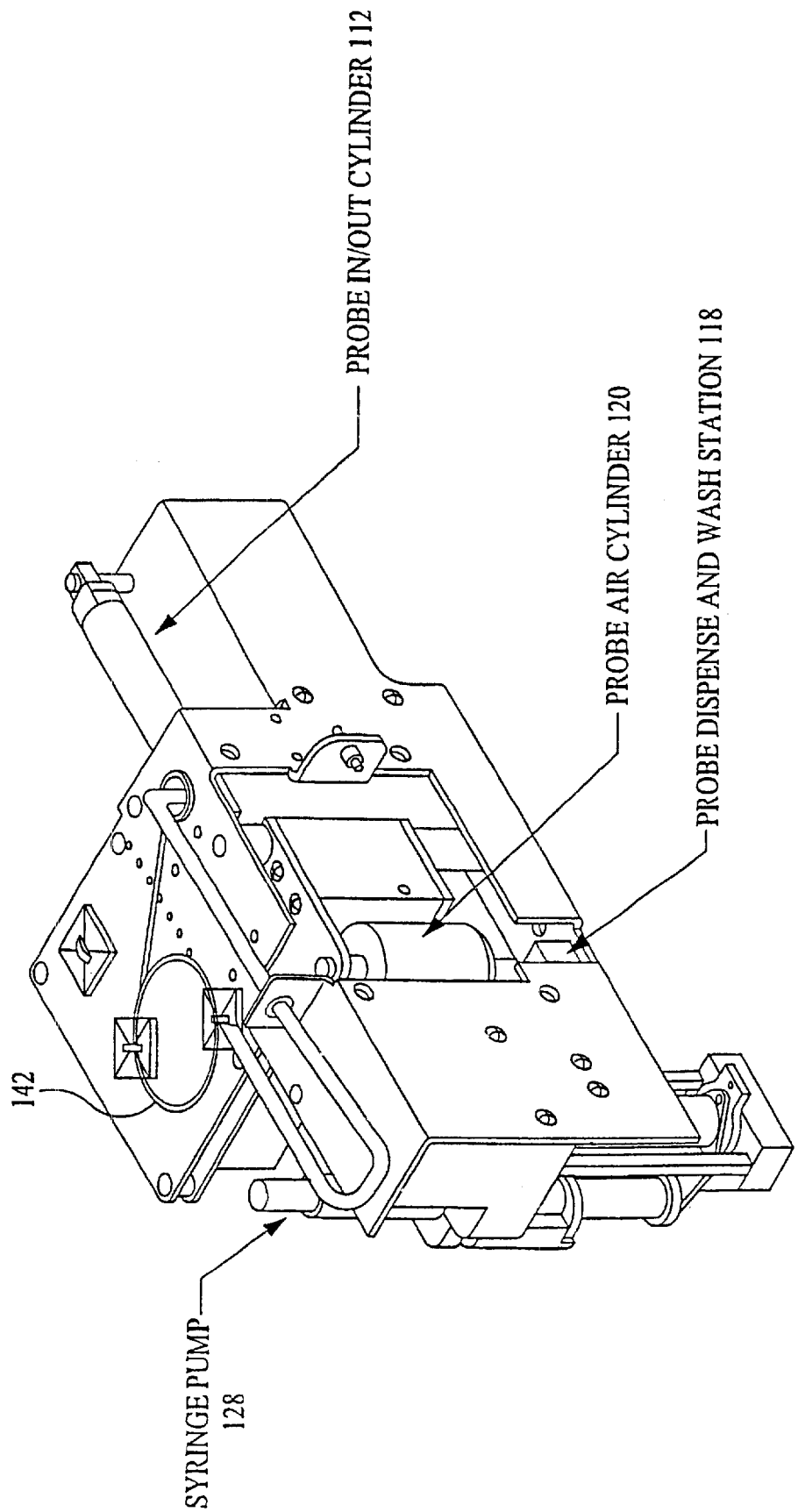
FIG. 6 is a perspective view of the air cylinders for the reagent delivery system of FIG. 2.

FIG. 6 is a perspective view of the air cylinders for the reagent delivery system of FIG. 2. Due to the need to avoid placing reagent into the plunger 129 of the syringe, the tubing 142 is of sufficient length so that any reagent will be contained within the tubing 142.

Use and Operation

Due to the operation of the biological reaction system, a multitude of reagents may be used. In order to avoid cross-contamination of the reagent vials, the vial inserts and the samples on the microscopes, the probe and probe dispense & wash station 118 should be cleaned after dispensing of a reagent. To accomplish this, wash buffer is used to clean the probe 119 and the probe dispense & wash station 118. As shown in FIG. 2, a probe purge liquid valve 102 and a probe wash liquid valve 100, both pressurized with wash buffer at 13 psi, are connected to the probe 119 and the probe dispense & wash station 118, respectively. A flow restrictor 122 limits the flow of wash buffer from the probe wash liquid valve and the probe dispense & wash station 118. The dispense control pcb 124, in combination with the microcontroller 30, controls the operation of the probe purge liquid valve 102 and the probe wash liquid valve 100. In practice, after the reagent is dispensed onto the microscope slide 114, the carrousel 44 is advanced so that the probe 119 and probe dispense & wash station 118 are in between slides. Thereafter, the dispense control pcb 124, in combination with the microcontroller 30, turns on the probe purge liquid valve 102 and the probe wash liquid valve 100 so that both the probe 119 and the probe dispense & wash station 118 are rinsed with wash buffer. And, since the probe 119 and probe dispense & wash station 118 are in between slides, the wash buffer is deposited into the waste tub 58 instead of onto the slides in the carrousel 44. In a preferred embodiment, the probe 119 and the probe dispense & wash station 118 are cleaned when the probe 119 is inserted in the probe dispense & wash station 118. Moreover, the dispense control pcb 124, in combination with the microcontroller 30, alternates turning one valve on and then off, and then turning the other valve on and then off. For example, the dispense control pcb 124 turns on the probe purge liquid valve 102, waits a predetermined amount of time, as described subsequently, and then turns off the probe purge liquid.valve 102. Thereafter, the dispense control pcb 124, in combination with the microcontroller 30, turns on the probe wash liquid valve 100, waits a predetermined amount of time, as described subsequently, and then turns off the probe wash liquid valve 100. Alternatively, the dispense control pcb 124 may begin the cleaning by turning on the probe wash liquid valve 100 first. This alternating of the flow of wash buffer from the probe purge liquid valve 102 and the probe wash liquid valve 100 produces a scrubbing action which cleans the probe 119 and the probe dispense & wash station 118 more effectively. In an alternate embodiment, the probe purge liquid valve 102 and the probe wash liquid valve 100 may be turned on simultaneously in order to clean the probe 119 and the probe dispense & wash station 118.

An example of an operation of the machine is as follows: the instrument reagent carousel 38 rotates to position the reagent tray so that the required reagent vial is positioned beneath the reagent probe 119; the probe 119 is then inserted into the vial insert 132 and reagent is aspirated into tubing 142 above the probe by drawing liquid into the syringe 128; the probe 119 is then raised and rotated to a position above the probe dispense & wash station 118; the probe 119 is then lowered in the probe dispense & wash station 118; the probe dispense & wash station 118 is connected to a piece of tubing 170 which is routed within the instrument such that the exit end of the tubing 170 is just above the microscope slide 114; when the probe 119 is down and seated into the probe dispense & wash station 118, the syringe pump 129 is reversed and the reagent is dispensed onto the microscope slide 114. As such, the reagent dispense system is designed to permit the sequential application of precise amounts of various reagents onto patient samples on glass microscope slides within the instrument.

Figure 7A:
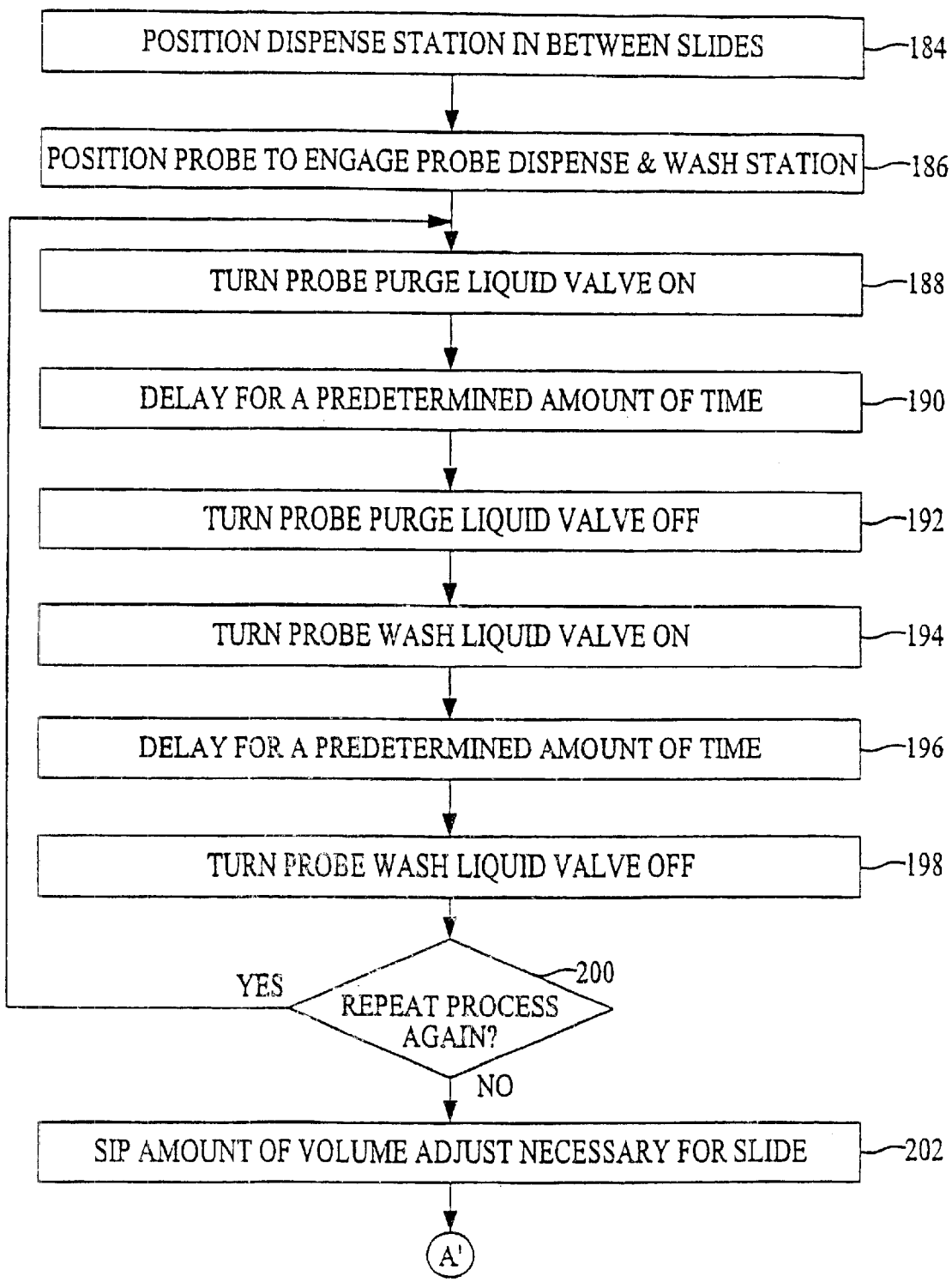
FIG. 7 is a flow chart of an example of the operation of the reagent delivery system of FIG. 2.
Figure 7B:
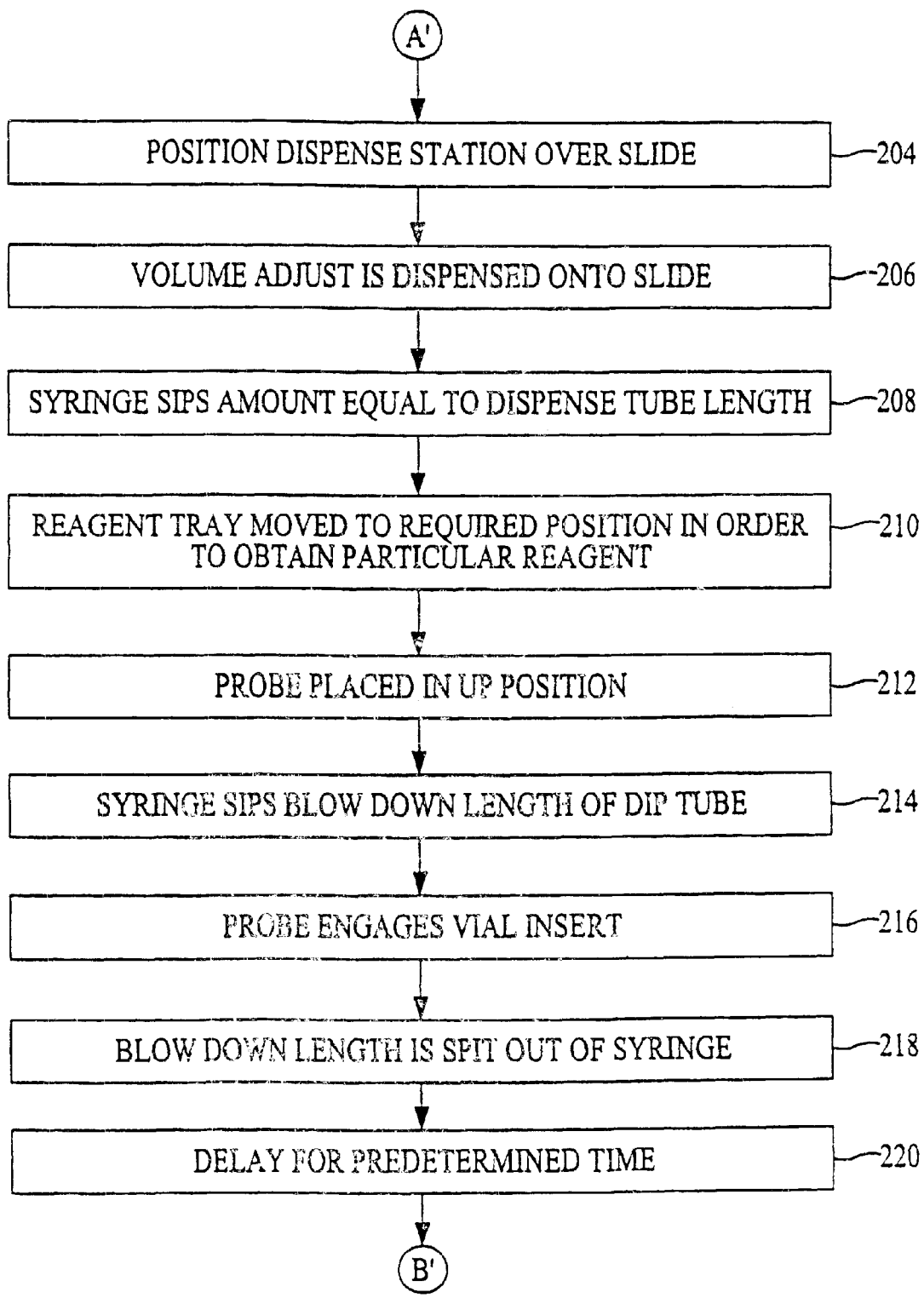
Figure 7C:
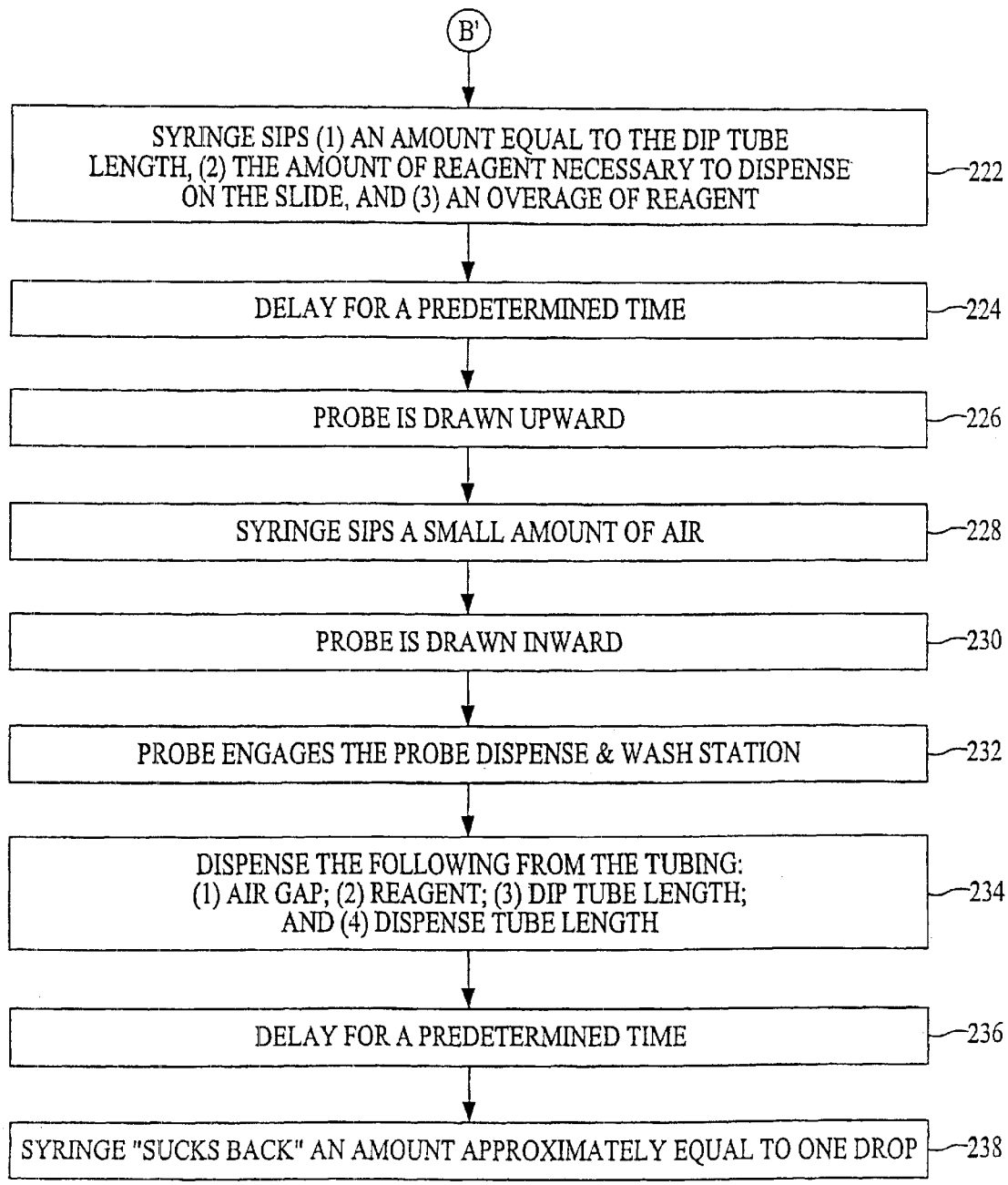
Figure 8A:
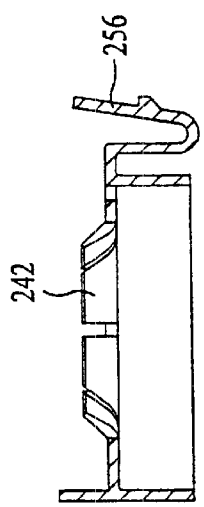
FIGS. 8a–d is a cross section, side, bottom, and top view of the reagent h older as shown in FIG. 3.
Figure 8B:
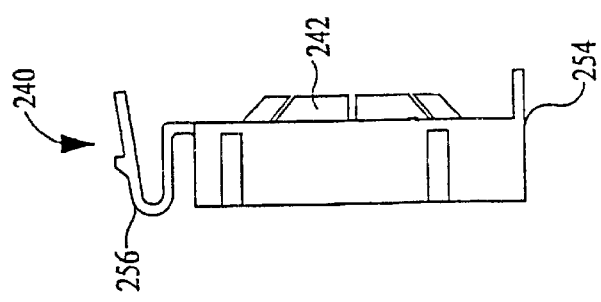
Figure 8D:
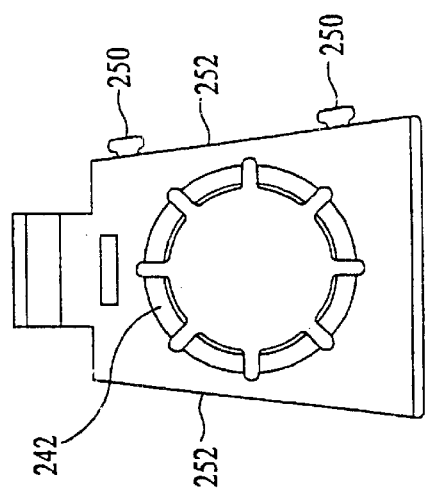
Figure 8C:
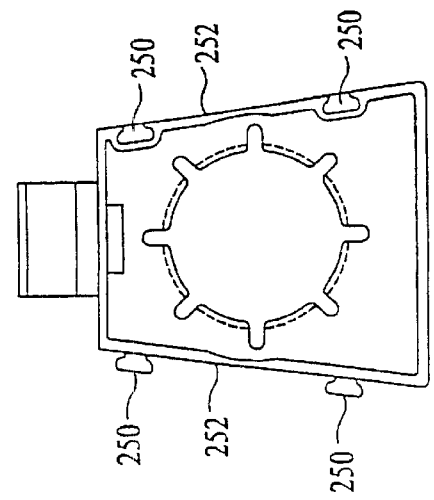

Referring to FIG. 7, there is shown a detailed flow chart of an example of the operation of the reagent delivery system of FIG. 2. Blocks 186–200 relate to the steps for washing the probe and the probe dispense & wash station 118. Simultaneously with the wash probe macro, the reagent tray is moved in anticipation of obtaining the particular reagent. At block 184, the dispense station is positioned in between slides. In a preferred embodiment, the slide is indexed by ½ of a position. This is so that any wash buffer which is used to clean the probe and the probe dispense & wash station 118 falls into the waste tub instead of onto one of the slides. At block 186, the probe is placed in the proper position to engage the probe dispense & wash station 118 (i.e., the probe down air valve 108 and the probe in air valve 106 are activated). At block 188, the probe purge liquid valve is turned on, thereby sending wash buffer through the tubing to the probe. At block 190, a delay block is entered for a predetermined amount of time (in a preferred embodiment for 2 seconds). At block 192, the probe purge liquid valve is turned off, thereby stopping wash buffer through the tubing to the probe. At block 194, the probe wash liquid valve is turned on, thereby sending wash buffer through the tubing to the probe dispense & wash station 118. At block 196, a delay block is entered for a predetermined amount of time (in a preferred embodiment for 1 second). At block 198, the probe wash liquid valve is turned off, thereby stopping wash buffer through the tubing to the probe dispense & wash station 118. At block 200, it is determined whether the wash macro is repeated. If so, block 188 is entered. In a preferred embodiment, the second sequence of alternating washing includes the steps of turning on the probe purge liquid valve, delaying for 0.59 seconds, and then turning off the probe purge liquid valve. Thereafter, the probe wash liquid valve is turned on, delayed for 0.50 seconds, and then turned off. This alternating of the activation of the probe purge liquid valve and the probe wash liquid valve allows for a scrubbing action, thereby cleaning the probe and the probe dispense & wash station 118 more effectively. Also, the delay times in between activation of the valves is decreased during the sequence of washings. Moreover, this alternating action may be for two cycles, as disclosed in FIG. 3, or may be for any number of cycles, depending on time constraints. Further, in the preferred embodiment, the alternating action begins with turning on the probe purge liquid valve. In an alternate embodiment, the alternating action may begin with turning on the probe wash liquid valve.

At block 202, the amount of volume adjust necessary for the slide is sipped by the syringe. Typically in processing of slide samples, a certain amount of wash buffer is necessary in order to process the sample. The wash buffer may be introduced to the sample in a variety of ways, one of which is through a syringe. At block 204, the dispense station is positioned over the slide. In a preferred embodiment, the slide position is indexed by ½ of a position. This is so that the probe dispense & wash station 118 is positioned properly over the slide.

At block 206, the volume adjust obtained at block 202 is dispensed onto the slide. This is accomplished by the processor turning on the motor to push the plunger of the syringe. At block 208, the syringe sips an amount equal to the dispense tube length, which is the tubing that directs fluid from the probe dispense & wash station 118 onto the slide. This is performed by turning on the motor to pull the plunger of the syringe and is done in order to avoid dripping onto the slide. At block 210, the reagent tray is moved to the required position in order to obtain the particular reagent. At block 212, the probe is placed in its up position. This is done by deactivating the probe down air valve 108 and allowing the spring return for the air cylinder to push the probe upward. At block 214, the syringe sips the blow down length of the dip tube. As shown previously with respect to FIG. 3, the reagent vial 116 has a dip tube 156 inside of it. Due to different levels of reagent in different reagent vials, the dip tube may be filled to different amounts. In order to consistently draw reagent from each reagent vial, air is forced into the syringe with an amount at least equal to the internal volume of the dip tube. As shown in FIG. 3, the dip tube has a predetermined internal volume. In this manner, the tube in each reagent vial is filled with air prior to drawing reagent from the dip tube. Thus, each reagent vial begins with a dip tube filled with air, regardless of whether the reagent vial is full or almost empty, so that a consistent amount of reagent may be drawn. In an alternate embodiment, the syringe may sip an amount less than the blow down length of the dip tube; however, the amount should be sufficient such that, for any reagent vial either filled or nearly empty with reagent, the dip tube should be filled with air after the air is forced into the dip tube. For example, the top of the dip tube is above the portion of the reagent vial which would contain reagent. Thus, a volume of air need only be forced into the dip tube for the portion of the dip tube which is below the fill line of the reagent vial.

At block 216, the probe engages the vial insert, by turning on the probe out air valve 104 and by turning on the probe down air valve 108. At this point, the probe is engaged with the vial insert for the particular reagent, as described subsequently. At block 218, the vial blow down length is spit out of the syringe in order to fill the dip tube with air, as discussed previously. At block 220, the system delays for a predetermined amount of time (in a preferred embodiment for 0.15 seconds). This delay allows the system equilibrate itself. Because of the use of plastics in the system (such as the reagent vial), the system has a certain amount of elasticity. In order to avoid inaccuracies, the process is delayed in order for the system to settle.

At block 222, the syringe sips (1) an amount equal to the dip tube length (which is air due to dip tube being previously evacuated), (2) the amount of reagent necessary to dispense on the slide, and (3) an overage of reagent. Sipping overage is necessary due to dilution of the reagent in the tubing. Due to using wash buffer in previous cycles, residual wash buffer is still in the tubing of the syringe since as wash buffer is pulled out, residual wash buffer remains. This residual wash buffer in the tubing dilutes the reagent which is sipped into the tubing. Therefore, an overage of reagent equal to 10% is sipped. At block 224, the system delays for a predetermined amount of time (in a preferred embodiment 1 second) in order for the system to equalize and the reagent to settle in the tubing of the syringe. At block 226, the probe disengages the vial insert when the probe is drawn upward. And immediately thereafter, the motor for the syringe sips a small amount of air, as shown at block 228. This is due to the fact that upon drawing the probe upward, a droplet of reagent may be at the end of the probe. In order to avoid contamination of the slides, the droplet is sipped upward. At block 230, the probe is drawn inward by activation of the probe in air valve 106.

At blocks 232–234, the reagent is dispensed. At block 232, the probe engages the probe dispense & wash station by placed the probe downward into the probe dispense & wash station 118. At block 234, the motor for the syringe is activated so that the following amounts may be dispensed: (1) air gap (which was sipped up at block 222 in order to remove droplet at the end of the probe); (2) reagent (which was sipped up at block 222; note that the overage is not dispensed); (3) dip tube length; and (4) dispense tube length (which is the tube between the probe dispense & wash station 118 and the slide). At block 236, there is a delay for a predetermined amount of time (in the preferred embodiment 1.5 seconds) in order for the system to equalize. At block 238, the syringe "sucks back" an amount approximately equal to one drop (e.g., 25 μL). This is due to the fact that a droplet may be at the end of the tubing 170 above the slide. And, when the probe dispense & wash station 118 moves, along with the tubing 170, the droplet above the tubing may drop onto another slide. This "suck back," which withdraws the droplet, therefore allows for more accurate and more consistent dispensing of reagents.

Referring to FIGS. 8a–d, there is shown a cross section, side, bottom, and top view of the reagent holder. At the right hand side of the reagent holder is a flat surface 254 for affixing a barcode flag. On the left hand side is a U-shaped member 256 which abuts against the reagent tray 36, as shown in FIG. 1a, thereby keeping the reagent vial and the barcode flag in a fixed position. In addition, there is a locking tab which abuts the U-shaped member which keeps the reagent vial from moving upward. In this manner, the reagent vial and barcode flag is kept in a fixed position.

In order to maintain a proper position of the reagent vial in the reagent carousel 38, the reagent vial should be fixed in position. A collar 242, as part of the reagent holder 240, holds the reagent vial in place. The neck 246 of the reagent vial is pushed through the collar 242, as shown in FIG. 3, to form a snap fit, so that a ledge 248 abuts the top of the collar 242. In addition, the reagent holder has interlocking tabs 250 so that separate reagent vials may be attached together. And, to the angle of the side portions 252 of the reagent holder 240, the reagent vials, when attached by the interlocking tabs 250, form a curve, which follows the curve of the reagent tray 36. Thus, a series of reagent vials 116, interlocked with the reagent holders 240, may be placed directly on the reagent tray 36.

From the foregoing detailed description, it will be appreciated that numerous changes and modifications can be made to the hardware and software aspects of the invention without departure from the true spirit and scope of the invention. For example, the present invention is not dependent on any specific type of computer architecture or type of protocol. This true spirit and scope of the invention is defined by the appended claims, to be interpreted in light of the foregoing specification.

We claim:

1. Dispensing reagent device comprising:
   a probe having at one end a shaped surface with a hole;
   tubing connected to the hole of the probe; and
   a probe dispense station having a recessed surface with an upper portion and a lower portion, the lower portion of the recessed surface having a hole,
   wherein the hole of the probe dispense station is proximate to, but not touching, the hole of the probe when at least a portion of the probe contacts at least a portion of the probe dispense station.

2. Dispensing reagent device as claimed in claim 1 wherein the shaped surface of the probe is hemispherical and wherein at least a portion of the upper portion of the probe dispense station is hemispherical.

3. Dispensing reagent device as claimed in claim 1 wherein at least a portion of the probe is composed of a pliable material.

4. Dispensing reagent device as claimed in claim 3 wherein the portion of the probe that is composed of a pliable material is an o-ring.

5. Dispensing reagent device as claimed in claim 1, further comprising tubing connected to the hole of the probe dispense station.

6. Dispensing reagent device as claimed in claim 1, wherein the hole of the probe is directly above the hole of the probe dispense station when the probe contacts the probe dispense station.

7. Dispensing reagent device as claimed in claim 1, wherein an annular seal is formed between the probe and the probe dispense station when the probe contacts the probe dispense station.

8. Dispensing reagent device as claimed in claim 1, wherein the one end of the probe is curved in shape and wherein the recessed surface of the probe dispense station is curved in shape.

9. Dispensing reagent device as claimed in claim 8, wherein the curved shape of the one end of the probe has a radius,
   wherein the curved shape of the recessed surface has a radius, and
   wherein the radius of the curved shape of the recessed surface is greater than the radius of curved shape of the one end of the probe.

10. Dispensing reagent device comprising:
    a probe having at one end a shaped surface with a hole;
    tubing connected to the hole of the probe; and
    a probe dispense station having a recessed surface with an upper portion and a lower portion, the lower portion of the recessed surface having a hole,
    wherein at least a portion of the shaped surface of the probe contacts the probe dispense station at the upper portion of the recessed surface, the shaped surface of the probe not contacting the recessed surface of the probe dispense station at the lower portion of the recessed surface,
    wherein the probe dispense station further has a trough, the trough adjacent to the upper portion of the probe dispense station.

11. Dispensing reagent device as claimed in claim 10 wherein the trough spirals downward.

12. Dispensing reagent device as claimed in claim 10, wherein the hole of the probe dispense station is proximate to, but not touching, the hole of the probe.

13. Dispensing reagent device as claimed in claim 10, further comprising tubing connected to the hole of the probe dispense station.

14. Dispensing reagent device comprising:
    a probe having at one end a shaped surface with a hole;
    tubing connected to the hole of the probe; and
    a probe dispense station having a recessed surface with an upper portion and a lower portion, the lower portion of the recessed surface having a hole,
    wherein at least a portion of the shaped surface of the probe contacts the probe dispense station at the upper portion of the recessed surface, the shaped surface of the probe not contacting the recessed surface of the probe dispense station at the lower portion of the recessed surface,
    wherein the probe dispense station further has a second hole in the upper portion, the second hole connected to tubing for sending wash buffer to the upper portion of the vial dispense station.

15. Dispensing reagent device as claimed in claim 14, wherein the hole of the probe dispense station is proximate to, but not touching, the hole of the probe.

16. Dispensing reagent device as claimed in claim 14, further comprising tubing connected to the hole of the probe dispense station.

17. Dispensing reagent device as claimed in claim 14, further comprising:
- a first valve connected to the tubing for sending wash buffer to the upper portion of the probe dispense station;
- a second valve connected to the tubing connected to the hole of the probe; and
- a processor controlling the first and second valves.

18. Dispensing reagent device as claimed in claim 17, wherein the processor controls the valves so that one valve of the first and second valves is opened and then closed and then another valve of the first and second valve is opened and then closed.

19. Dispensing reagent device as claimed in claim 18, wherein the processor controls the one valve so that the one valve is opened for a first predetermined time and then closed,
- thereafter, the processor controls the another valve so that the another valve is opened for a second predetermined time and then closed,
- thereafter, the processor controls the one valve so that the one valve is opened for a third predetermined time and then closed, and
- thereafter, the processor controls the another valve so that the another valve is opened for a fourth predetermined time and then closed,
- the first predetermined time being greater than the third predetermined time and the second predetermined time being greater than the fourth predetermined time.

20. Dispensing reagent device as claimed in claim 19, wherein the first predetermined time is greater than the second predetermined time, the second predetermined time is greater than the third predetermined time, and the third predetermined time is greater than the fourth predetermined time.

21. Dispensing reagent device comprising:
- a probe having at one end a shaped surface with a hole;
- tubing connected to the hole of the probe;
- a probe dispense station having a recessed surface with an upper portion and a lower portion, the lower portion of the recessed surface having a hole; and
- tubing connected to the hole in the probe dispense station,
- wherein the at least a portion of the shaped surface of the probe contacts the probe dispense station at the upper portion of the recessed surface, the shaped surface of the probe not contacting the recessed surface of the probe dispense station at the lower portion of the recessed surface.

22. Reagent dispense system comprising:
- probe having a hole;
- tubing connected to the hole of the probe;
- means for moving fluid within the tubing;
- vial dispense station having an upper surface with a hole, the probe contacting a portion of the upper surface, the hole of the probe dispense station being proximate to, but not touching, the hole of the probe when at least a portion of the probe contacts at least a portion of the probe dispense station;
- tubing connected to the hole of the vial dispense station; and
- means for moving the probe and the vial dispense station relative to one another to engage the probe with the vial dispense station.

23. Reagent dispense system as claimed in claim 22 wherein the means for moving fluid within the tubing includes:
- a syringe having a plunger, the syringe connected to the tubing; and
- a motor connected to the plunger.

24. Reagent dispense system as claimed in claim 22 wherein the upper surface of the vial dispense station is hemispherical and wherein the probe is hemispherical at one end.

25. Reagent dispense system as claimed in claim 24 wherein at least a portion of the probe is composed of a pliable material.

26. Method of dispensing reagent comprising the steps of:
- providing a probe having a lower surface, a probe dispense station with an upper surface with a hole, and tubing connected to the probe dispense station;
- engaging the lower surface of the probe with the upper surface of the probe dispense station to form a seal between at least a portion of the lower surface of the probe with a portion of the upper surface of the probe dispense station, the lower surface of the probe not contacting the hole of the probe dispense station;
- dispensing reagent through the tubing; and
- disengaging the lower surface of the probe from the portion of the upper surface of the probe dispense station.

27. Method of dispensing reagent as claimed in claim 37 wherein the upper surface of the probe dispense station is recessed,
- wherein the hole is at a lowermost portion of the upper surface, and
- wherein the step of engaging the lower surface of the probe with the upper surface of the probe dispense station includes contacting a pliable surface on the probe with the portion of the upper surface of the probe dispense station.

28. Method of dispensing reagent as claimed in claim 26 further comprising the step of cleaning at least the lower surface of the probe and the upper surface of the probe dispense station prior to the step of disengaging the lower surface of the probe from the upper surface of the probe dispense station.

29. Method of dispensing reagent as claimed in claim 26 wherein the step of engaging the lower surface of the probe with the upper surface of the probe dispense station includes contacting the lower surface of the probe with the upper surface of the probe dispense station to form an annular seal.

30. Method of dispensing reagent as claimed in claim 26 wherein the step of disengaging the lower surface of the probe from the portion of the upper surface of the probe dispense station includes moving the probe and the probe dispense station relative to one another so that the probe is above the probe dispense station, and
- further comprising withdrawing an amount at least equal to one drop of liquid from the hole in the probe immediately after the step of moving the probe and the vial insert relative to one another.

31. Method of cleaning a probe and probe dispense station comprising the steps of:
- providing the probe having a lower surface, the probe dispense station with an upper surface and tubing, the upper surface having a first hole and a second hole, the first hole at a lowermost portion of the upper surface, the second hole connected to the tubing;
- engaging the lower surface of the probe with the upper surface of the probe dispense station to form a seal between at least a portion of the lower surface of the probe with at least a portion of the upper surface of the probe dispense station and to form a cavity between the lower surface of the probe and the upper surface of the probe dispense station, the cavity containing the first and second holes of the upper surface;

cleaning at least the lower surface of the probe and the upper surface of the probe dispense station by sending fluid through the tubing connected to the second hole; and disengaging the lower surface of the probe from the upper surface of the probe dispense station.

32. Method of cleaning a probe and probe dispense station as claimed in claim 31 wherein the lower surface of the probe has a hole and further comprising the step of cleaning at least the lower surface of the probe and the upper surface of the probe dispense station by sending fluid through the tubing connected to the hole in the probe.

33. Method of cleaning a probe and probe dispense station as claimed in claim 32 wherein the step of cleaning by sending fluid through the tubing connected to the second hole and the step of cleaning by sending fluid through the tubing connected to the hole in the probe are alternated.

* * * * *